US006867032B2

(12) United States Patent
Shimizu et al.

(10) Patent No.: US 6,867,032 B2
(45) Date of Patent: Mar. 15, 2005

(54) ENZYMATIC UNHAIRING AGENT FOR USE IN TANNING FOR PRODUCING LEATHER AND METHOD FOR ENZYMATIC UNHAIRING TREATMENT

(75) Inventors: Yasuhiro Shimizu, Hikone (JP); Atsushi Sugiyama, Shiga (JP); Akira Ohta, Kakogawa (JP)

(73) Assignee: Daiwa Kasei K.K., Osaka (JP)

( * ) Notice: Subject to any disclaimer, the term of this patent is extended or adjusted under 35 U.S.C. 154(b) by 186 days.

(21) Appl. No.: 10/149,026

(22) PCT Filed: Dec. 5, 2000

(86) PCT No.: PCT/JP00/08605

§ 371 (c)(1), (2), (4) Date: Jun. 3, 2002

(87) PCT Pub. No.: WO01/42513

PCT Pub. Date: Jun. 14, 2001

(65) Prior Publication Data

US 2002/0182711 A1 Dec. 5, 2002

(30) Foreign Application Priority Data

Dec. 6, 1999 (JP) .......................................... 11-346267

(51) Int. Cl.[7] ............................ C12N 9/52; C12N 1/20; C14C 1/00; C12S 9/00

(52) U.S. Cl. .................... 435/220; 435/253.5; 435/265; 510/392

(58) Field of Search .............................. 435/220, 253.5, 435/265; 510/392

(56) References Cited

U.S. PATENT DOCUMENTS

| | | | | |
|---|---|---|---|---|
| 3,840,433 A | | 10/1974 | Aunstrup et al. | 435/265 |
| 4,288,556 A | | 9/1981 | Belloc et al. | 435/265 |
| 5,508,195 A | | 4/1996 | Christner et al. | |
| 6,156,557 A | * | 12/2000 | Moriyama et al. | 435/223 |

FOREIGN PATENT DOCUMENTS

| | | |
|---|---|---|
| GB | 1 084 213 | 9/1967 |
| JP | 2000-60547 | 2/2000 |
| SU | 1715840 | 2/1992 |
| WO | WO 94/06942 | 3/1994 |

* cited by examiner

*Primary Examiner*—Jean C. Witz
*Assistant Examiner*—Susan Hanley
(74) *Attorney, Agent, or Firm*—Knobbe, Martens, Olson & Bear LLP

(57) ABSTRACT

The invention provides an enzymatic unhairing agent for use in an unhairing step in tanning for producing leather comprising an alkaline protease as an active component; a treatment solution comprising a pH-adjusting agent and the enzymatic unhairing agent; a method for enzymatic unhairing treatment in tanning for producing leather comprising contacting the treatment solution with a raw hide or skin; and a leather thus produced. According to the invention, it is attained markedly reduction of the pollution load in the unhairing waste water and leather and recovered hairs both of good quality can be obtained.

10 Claims, No Drawings

ENZYMATIC UNHAIRING AGENT FOR USE IN TANNING FOR PRODUCING LEATHER AND METHOD FOR ENZYMATIC UNHAIRING TREATMENT

FIELD OF THE INVENTION

The present invention relates to an enzymatic unhairing agent for use in tanning for producing leather, and more particularly to an enzymatic unhairing treatment solution for use in an unhairing step in tanning for producing leather and a method for enzymatic unhairing treatment using the unhairing treatment solution.

BACKGROUND ART

A sequence of steps for tanning animal hides and skins such as cowhide is roughly divided into three steps: preparative step, tanning step and finishing step. The preparative step generally comprises soaking a raw hide in water, fleshing, unhairing and liming, splitting, scudding, re-liming, deliming and bating although slightly different depending on the kind of leather to be produced, the kind of tanning step subsequent to the preparative step, and the like.

Currently, the unhairing and liming operation in leather tanning are continuously carried out in a drum or a paddle using concentrated calcium hydroxide and sulfide as unhairing agent to reduce the operation time and to shorten the operations (hair-burn method). More specifically, the hide is softened on absorption of water in the water-soaking operation, and is immersed in milk of lime containing sodium sulfide or sodium hydrogensulfide serving as an unhairing accelerator. As a result, the epidermal tissue is decomposed and separated from the corium, and the hair root is loosened to facilitate unhairing while the hairs are decomposed and dissolved due to the action of the unhairing accelerator.

However, this method permits decomposition and dissolution of hairs, making it impossible to recover the hairs, so that the waste water invariably contains a large amount of keratin decomposition products derived from the dissolved hairs together with concentrated calcium hydroxide and sulfide, which would be likely to cause significant environmental pollution. Further, this involves a serious drawback that the disposal of the waste water necessitates large-scale facilities and incurs high costs.

In recent years, in order to overcome the drawback encountered in the hair-burn method and to reduce the pollution load of waste water, a hair-saving unhairing method was proposed which is intended, based on the hair-burn method, to protect the hair body portion against the decomposition occurring due to the unhairing agent. Typical examples of the proposed methods include BLAIR Method [Leather, 1998 (Feb.):23–26 (1988)] and SIROLIME Method [Cranstone, R. W., Davis, M. H., Scroggie, J. G., J.S.L.T.C., 70, 50–55 (1986)].

However, even these proposed methods are still unsatisfactory in the effect of reducing the pollution load of waste water. Further, the SIROLIME Method has a shortcoming that hydrogen sulfide gas and chlorine gas are given off from sodium hydrogensulfide and hypochlorite used, necessitating their disposal and posing a problem of adversely affecting the leather surface, which referred to as silver surface, to give a defect.

DISCLOSURE OF THE INVENTION

The present inventors conducted extensive research to achieve an object of providing an unhairing treatment technique which, mainly from the viewpoints of overcoming the environmental pollution problem and effectively using resources, is capable of markedly reducing the pollution load of unhairing waste water and capable of recovering hairs, and which is capable of suppressing the use of an unhairing agent such as calcium hydroxide and sulfide, i.e. strong alkali, to a maximum extent in comparison with the conventional hair-burn methods, and capable of achieving high workability, the method being drastically innovative in an unhairing step in tanning for producing leather.

As a result, the inventors found that an unhairing treatment technique which complies with the foregoing object can be provided by using an alkaline protease. The invention was accomplished based on this finding.

The invention provides an enzymatic unhairing agent for use in an unhairing step in tanning process for producing leather comprising an alkaline protease as an active component.

More specifically, the invention provides the unhairing agent wherein the alkaline protease has a keratin-hydrolyzing activity of 0.05 or more; the unhairing agent wherein the alkaline protease has a keratin-hydrolyzing activity of 0.2 or more; the unhairing agent wherein the alkaline protease is the one derived from Actinomycetes; and the unhairing agent wherein the alkaline protease is the one produced by *Streptomyces sp.* TOTO-9805 (FERM BP 6359).

The invention also provides a treatment solution for use in an unhairing step in tanning process for producing leather comprising a pH-adjusting agent and the enzymatic unhairing agent; the treatment solution wherein the pH-adjusting agent is calcium hydroxide and the pH of the solution is adjusted to a range of 10 to 12; the treatment solution wherein the concentration of calcium hydroxide is 0.2 to 0.8%; the treatment solution wherein the pH-adjusting agent is calcium hydroxide and sodium hydrogensulfide, and the pH of the solution is adjusted to a range of 10 to 12; and the treatment solution wherein the concentration of calcium hydroxide is 0.2 to 0.8% and the concentration of sodium hydrogensulfide is 0.2 to 0.8%.

The invention further provides a method for enzymatic unhairing treatment in tanning for producing a leather comprising contacting the enzymatic unhairing treatment solution with a raw hide or skin; and the method for enzymatic unhairing treatment in tanning for producing a leather wherein the contact is carried out using a treatment solution comprising an alkaline protease having an activity of 15 to 150 APU/g under conditions of a bath ratio of 1:2–4, a temperature of 20 to 30° C. and a pH of 10 to 12 for 12 to 24 hours.

The invention further provides a method for recovering the removed hairs in tanning for producing leather wherein the recovery is performed after the enzymatic unhairing treatment; a method for producing a leather by conducting the method for enzymatic unhairing treatment; and a leather thus produced.

According to the enzymatic unhairing method using the treatment solution containing the enzymatic unhairing agent of the invention, the amount of calcium hydroxide used can be reduced by about 1/10 or less compared with the hair-burn method heretofore carried out. In addition, the method of the invention permits reduction in the amount of sulfide used by about 1/5 or less. Based on these features, the method of the invention can markedly decrease the amounts of lime and sulfide in the unhairing waste water produced in the unhairing step in tanning for producing leather. The dissolution of hairs rarely occurs in the unhairing step and most of removed hairs can be recovered. This means that the amount of decomposition products of hair protein in the unhairing waste water can be significantly lowered. In other words, the method of the invention permits marked reduction in BOD, COD, sulfide contents, sludge amounts and the like of the unhairing waste water.

According to the practice of the invention, for example, the amount of sludge required in activated sludge process can be strikingly reduced in disposal of unhairing waste water, so that the treatment of waste water disposal can be more simply done. Furthermore, the waste water disposal can be satisfactorily carried out by use of conventional equipment without a need to use special facilities nor additional mechanical means for unhairing.

According to the invention, hairs are pulled off at the hair root without leaving a trace of hair root looking like black spots. Therefore the leather surface is glossy smooth and aesthetically favorable and presents a soft finished surface without adverse influence on the silver surface. In view of these aspects, the unhairing treatment method of the invention is advantageous from the practical viewpoints in that in addition to reduction in the load of waste water disposal, a leather of good quality can be obtained and the hairs can be recovered.

Detailed description is given below about the enzymatic unhairing agent of the invention, the unhairing treatment solution containing the unhairing agent and the unhairing method using the solution in this order.

The enzymatic unhairing agent of the invention essentially contains alkaline protease as the active component. Species of the alkaline protease are not limited. However, for example, preferred are those having a keratin-hydrolyzing activity of about 0.05 to about 0.30, and more preferred are those having a keratin-hydrolyzing activity of about 0.2 to about 0.22.

The keratin-hydrolyzing activity is defined as follows. 1 ml of an enzyme solution having an activity adjusted to 50 APU/ml is mixed with 1 ml of 100 mmol/l borax-sodium carbonate buffer solution (pH 10.5) containing 2% of keratin particles (product of Tokyo Kasei Co., Ltd.) having adjusted particle sizes ranging from 0.053 to 0.105 mm by sieving. Then the mixture is reacted at 35° C. for 60 minutes. 2 ml of 7.2% trichloroacetic acid solution is added to terminate the reaction. Then the mixture is allowed to stand at 35° C. for 20 minutes, and is passed through filter paper (ADVANTEC, No. 6, product of TOYO Co., Ltd.) to give a protein decomposition product in the filtrate. The keratin-hydrolyzing activity is expressed in terms of increased amount (the increased amount being calculated based on the measured value at 660 nm at reaction time zero) of absorbency obtained at 660 nm by measuring the amount of protein decomposition product in the filtrate by the Folin method.

The titer of the enzyme solution (APU/ml) is obtained as follows. 1 ml of an enzyme solution is mixed with 1 ml of 100 mmol/l borax-sodium carbonate buffer solution (pH 10.5) containing 1% of Hammarsten's milk casein. The mixture is reacted at 35° C. for 10 minutes, and 2 ml of 7.2% trichloroacetic acid solution is added to terminate the reaction. The mixture is allowed to stand at 35° C. for 20 minutes, and is passed through filter paper (ADVANTEC, NO. 6, product of TOYO Co., Ltd.) to give a protein decomposition product in the filtrate. The titer of the enzyme solution is obtained by taking the amount of enzyme (which releases 1 $\mu$g of tyrosine per 1 minute) as 1 APU in the method of measuring the casein-hydrolyzing activity in which the protein decomposition product in the filtrate is measured by the Folin method.

The contemplated effect of the invention, especially the remarkable unhairing effect, can be achieved by use of alkaline protease having such keratin-hydrolyzing activity presumably for the following reason. The enzyme acts on the hair root loosened by the action of calcium hydroxide, and decomposes the keratin constituting the hair root, thereby facilitating the removal of hairs at the hair root.

The alkaline protease which is especially suitable in the invention is the one derived from Actinomycetes. Typical examples are those produced by *Streptomyces, sp.* TOTO-9805 strain which is a variant pertaining to alkaline *Streptomyces* genus.

The variant was deposited with National Institute of Bioscience and Human-Technology Agency of Industrial Science and Technology, 1–3, Higashi, 1-chome, Tsukuba-shi, Ibaragi-ken, Japan on May 19, 1998 under *Streptomyces sp.* TOTO-9805 and was registered under deposition number FERM BP-6359.

The cultivation of the above-mentioned microorganisms and the harvest of the contemplated alkaline protease can be done in the conventional manner. For example, the foregoing microorganism, which is alkaline Actinomycete, is cultivated in an alkali region wherein a suitable alkali is provided in a usual culture medium. A nutrition source such as carbon source, nitrogen source and other inorganic salt source which are used in the culture medium can be any of those usually used for cultivation of this kind of enzyme-producing microorganisms. Examples of the carbon source are glucose, soluble starch, cellulose and the like. Examples of the nitrogen source are nitrate, ammonium salt and like inorganic salts, urea, peptone, dried yeast, yeast extract, soybean powder, corn steeped liquor, casein, meat extract, amino acids, etc. Other inorganic salts include, for example, magnesium salt, potassium salt, sodium salt, phosphate, etc. These nutrition sources pertaining to each group can be used either alone or in optional combination. Examples of the alkali to be added to the culture medium are an aqueous solution of sodium carbonate, sodium hydrogencarbonate or like carbonates, an aqueous solution of sodium hydroxide, an aqueous solution of ammonia, all in a concentration of about 0.5 to about 2%, etc. The pH of the culture medium is preferably in the range of about 8 to about 11. The cultivation is aerobically conducted at a temperature of about 20 to about 35° C., preferably about 27 to about 35° C. for 2 to 5 days either by shaking or by agitation. The contemplated enzyme is secreted or accumulated mainly in the culture solution.

The contemplated enzyme can be easily harvested from the culture solution and purified by conventional methods utilizing the physicochemical properties of the enzyme. For example, a crude enzyme solution can be obtained by removing the cells through filtration, centrifuging or the like. The crude enzyme solution may be purified by conventional procedures such as salting-out, organic solvent sedimentation, ultrafiltration, gel filtration chromatography, ion exchange chromatography, hydrophobic chromatography and the like. A preferred purification method comprises, for example, adding 80% saturated ammonium sulfate to the culture filtrate for salting-out, dissolving the obtained precipitate in a buffer and conducting an ion exchange chromatography using CM-Toyopearl 650M (product of Toso Co., Ltd.), DEAE-Toyopearl 650M (product of Toso Co., Ltd.) or the like. This method permits preparation of SDS-electrophoretically uniform purified enzyme.

The enzymatic unhairing agent of the invention is usually prepared in the form of an unhairing treatment solution containing the above-specified enzyme and a pH-adjusting agent. The pH-adjusting agent to be used is not limited insofar as it is capable of adjusting the pH of the treatment solution to about 10 to about 12 which is suitable for unhairing treatment of hide. Generally it is preferred to use calcium hydroxide. Although the contemplated effect of the invention can be satisfactorily achieved by use of calcium hydroxide alone, calcium hydroxide may be used in combination with sodium hydrogensulfide to perform more complete unhairing.

The amounts (concentrations) of the enzymatic unhairing agent and the pH-adjusting agent in the unhairing treatment solution of the invention can be suitably determined according to the kind of raw hide to be treated therewith, the method for unhairing treatment, conditions, etc. and are not limited. The amount of enzymatic unhairing agent to be used is usually selected from a range of about 15 to about 150 APU/g, preferably about 20 to about 90 APU/g, more preferably about 30 to about 90 APU/g, based on the weight of raw hide. The amount of calcium hydroxide serving as the pH-adjusting agent is selected from a range of about 0.2 to about 0.8%, preferably about 0.4 to about 0.6%. When calcium hydroxide is used in combination with sodium hydrogensulfide, the amount of sodium hydrogensulfide to be combinedly used may be used in a concentration in the range of about 0.2 to about 0.8%, preferably about 0.4 to about 0.6%.

The unhairing treatment solution of the invention may further contain a surfactant, an antiseptic agent (such as “Sismoran BH”, product of Bayer AG, “Suplaran UF”, product of Zschimmer & Schwarz Co., Ltd.) and the like when so required. These additives are used in a conventional amount, usually about 0.1 to about 1%.

The unhairing treatment in tanning for producing leather according to the invention can be carried out by the conventional unhairing step (liming step) using a drum or a paddle and employing the unhairing treatment solution of the invention. For example, the unhairing treatment of the invention using a drum can be carried out by treating with the unhairing treatment solution of the invention a raw hide previously soaked in water in the conventional manner at a bath ratio of 1:2–5, preferably 1:2–4, a temperature of 18 to 30° C., preferably 20 to 30° C., more preferably 25 to 30° C., and a pH of 10 to 12 for about 3 to about 24 hours, preferably about 12 to about 24 hours.

The hide unhaired by the foregoing treatment is limed as usual and is tanned in the conventional manner, whereby the contemplated leather can be produced. When the enzymatic unhairing treatment method of the invention is employed, advantageously the treatment solution used in the subsequent liming treatment can be repeatedly used.

The hairs obtained by the enzymatic unhairing treatment of the invention are those unhaired by being pulled off at their hair root with substantially no decomposition or dissolution of hairs, so that the hairs can be easily recovered from the unhairing treatment solution by, e.g. filtration. The thus-recovered hairs are useful as fiber materials for producing felts, brushes or the like in the field of industrial materials and are expected for use as cosmetic materials, animal feed materials or the like.

Hides or skins of animal for which the method of the invention can be employed are typically of cows and bulls. Other animal examples include pigs, horses, sheep, goats and the like.

The unhairing treatment method of the invention has a high practical value, compared with conventional unhairing treatment methods, in that: (1) the method can reduce the amount of sodium sulfide, sodium hydrogensulfide or like sulfides in the unhairing waste water; (2) the calcium hydroxide solution to be used in the subsequent liming step can be repeatedly used so that the drain of calcium hydroxide into the waste water is limited only to calcium hydroxide adhering to the hide; (3) the removed hairs are substantially not dissolved in the treatment solution and most of them can be recovered, resulting in significant decrease of dissolved hairs and protein derived from dissolved hairs which otherwise would be included in the waste water; (4) the obtained leather is softer than the leather treated by conventional unhairing method, has an glossy smooth surface because even the hair root is removed, and allows to be dyed in a color of high brightness; and (5) the method permits omitting the bating step in tanning for producing a leather, and is capable of enhancing the yield.

BEST MODE FOR CARRYING OUT THE INVENTION

To clarify the invention in more detail, description is given below with reference to a Reference Example illustrating an example of preparation of alkaline protease according to the invention and Examples illustrating the unhairing treatment method of the invention. The percents in the Examples are all by weight based on the weight of raw hide. The titer of enzyme to be used and the activity measuring method are as described hereinbefore unless otherwise indicated.

REFERENCE EXAMPLE 1

Production of Crude Enzyme Preparation

Sakaguchi flask (500 ml-vol.) was charged with 100 ml of a culture medium (pH 9.0) containing 1.5% of soluble starch, 1.5% of skimmed milk, 0.3% of $K_2HPO_4$, 0.1% of yeast extract, 0.05% of $MgSO_4 \cdot 7H_2O$ and 1.0% of $NaHCO_3$ separately sterilized. A pre-seed culture medium (yeast-malt broth, pH 11) containing *Streptomyces sp.*, TOTO-9805 srain (FERM BP 6359) was inoculated and was cultured with shaking at 30° C. and 120 revolutions per minute for 5 days. After completion of cultivation, the culture medium was centrifuged at 8000 revolutions per minute for 10 minutes to remove the cells, whereby about 7600 ml of crude enzyme solution (26 APU/ml) was obtained.

Ammonium sulfate powder was added to the crude enzyme solution until the solution became 80% saturated. After standing 24 hours in a dark place at 5° C., the precipitate was recovered by centrifuging at 8000 revolutions per minute and was lyophilized, whereby 3.7 g of a crude enzyme preparation (14980 APU/g) was obtained.

EXAMPLE 1

A raw hide (hide of steer or hide of castrated bull) was soaked in water in a drum (a bath ratio of 1:3 at 25° C.) for 1 hour and washed with flowing water for 5 minutes. Then the raw hide was rotated at 25° C. for several hours in water containing 0.2% of “Sismoran BH” (product of Bayer AG) serving as a surfactant and an antiseptic agent, 0.1% of “Suplaran UF” (product of Zschimmer & Schwarz Co., Ltd.) serving as a surfactant for degreasing, and 0.2% of sodium carbonate. After standing overnight, the hide was immersed in water. Thereafter the water was stirred at a bath ratio of 1:3 at 25° C. for 10 minutes, and the hide was subjected to the following enzymatic unhairing treatment.

The above-water soaked hide was treated with stirring at 25° C. for 3 hours with a treatment solution containing 0.6% of sodium hydrogensulfide, 0.3% of calcium hydroxide (hydrated lime) and a specified amount of alkaline protease (one prepared above in Reference Example) having a titer of 30 to 90 APU/g per gram of the raw hide at a bath ratio of 1:3. Thereafter hydrated lime was added in an amount of 0.2% to adjust the pH value to 10 to 12 and the mixture was stirred for 4 hours to undergo an unhairing treatment. Standing until the next morning completed the unhairing treatment.

It turned out that a complete unhairing treatment was accomplished by using an enzyme having a titer of 30 APU/g per gram of the raw hide and that the removed hairs were recovered in the form of aegagropila. A complete unhairing treatment was achieved in 5 hours after start of unhairing treatment by using an enzyme having a titer of 90 APU/g.

EXAMPLE 2

A raw hide (hide of steer or hide of castrated bull) was soaked in water in a drum at a bath ratio of 1:3 at 25° C. for 2 hours and washed with flowing water for 5 minutes. Then the raw hide was rotated at a bath rate of 1:3 at 25° C. for several hours in water containing 0.2% of "Sismoran BH", 0.2% of "Suplaran UF", and 0.2% of sodium carbonate. After standing overnight, the hide was immersed in water. Further the water was stirred at a bath ratio of 1:2 at 25° C. for 10 minutes, and the hide was subjected to the following enzymatic unhairing treatment.

The above-obtained hide was treated with stirring at 25° C. for 3 hours using a treatment solution containing 0.5% of sodium hydrogensulfide, 0.3% of hydrated lime and alkaline protease (one prepared above in Reference Example) having a titer of 60 APU/g per gram of the raw hide at a bath ratio of 1:2. Thereafter hydrated lime was added in an amount of 0.2% to adjust the pH value to 10 to 12 and the mixture was stirred for 4 hours to undergo an unhairing treatment. Standing until the next morning completed the unhairing treatment, thereby giving an unhaired hide. By the above-mentioned procedure, 144 g of hairs were recovered from 5 kg of raw haide.

It is generally known that a raw hide contains about 45 g of hair protein per kilogram of raw hide (Japan Leather Technique Association, new edition "Leather Science", p.280, Nov. 25, 1992). On a calculation basis, the above-recovered hairs show a recovery ratio of about 64%. This means the following. As compared with the hair-burn method conventionally carried out in which the hairs are completely dissolved, not only the hairs can be recovered but also the inclusion of protein derived from hairs into waste water is reduced and the pollution load can be markedly lowered.

The above-obtained unhaired hide was immersed in 3% of hydrated lime at a bath ratio of 1:3 at 25° C. for 20 hours, and thereafter was subjected to splitting, deliming, pickling, chrome-tanning, shaving, neutralization, re-tanning, dyeing, oiling, samming, drying, conditioning, milling and toggling, whereby a leather was obtained.

The obtained leather was compared, in respect of appearance, with the comparison leather which was produced in the similar manner as described above after unhairing treatment (bath ratio of 1:2, 1.5% of sodium hydrogensulfide, 1.5% of sodium sulfide and 3% hydrated lime, 25° C., standing overnight) according to the hair-burn method conventionally employed.

The results show that the hide obtained according to the invention was soft, dyed in a brilliant color, and free from reduction in heat resistance, tearing strength and the like.

INDUSTRIAL APPLICABILITY

According to the invention, an unhairing treatment technique in an unhairing step in tanning for producing leather is provided. The unhairing treatment technique of the invention can markedly reduce the pollution load of the unhairing waste water, can recover the hairs, and is excellent in workability.

What is claimed is:

1. An enzymatic unhairing agent for use in an unhairing step in tanning for producing leather comprising an alkaline protease produced by *Streptomyces sp.* TOTO-9805 strain (FERM BP 6359) as an active component.

2. A treatment solution for use in an unhairing step in tanning for producing leather comprising the enzymatic unhairing agent of claim 1 together with a pH-adjusting agent.

3. The treatment solution according to claim 2, wherein the pH-adjusting agent is calcium hydroxide and the pH of the solution is adjusted to a range of 10 to 12.

4. The treatment solution according to claim 3, wherein the concentration of calcium hydroxide is 0.2 to 0.8%.

5. The treatment solution according to claim 2, wherein the pH-adjusting agent is a combination of calcium hydroxide and sodium hydrogensulfide, and the pH of the solution is adjusted to a range of 10 to 12.

6. The treatment solution according to claim 5, wherein the concentration of calcium hydroxide is 0.2 to 0.8%, and the concentration of sodium hydrogensulfide is 0.2 to 0.8%.

7. A method for enzymatic unhairing treatment in an unhairing step in tanning for producing leather comprising contacting the treatment solution for use in an unhairing step in tanning for producing leather according to claim 2 with a raw hide or skin.

8. The method according to claim 7, wherein the step of contacting the treatment solution is carried out for 12 to 24 hours using a treatment solution containing alkaline protease having an activity of 15 to 150 APU/g under the conditions of a bath ratio of 1:2–4, a temperature of 20 to 30° C. and a pH of 10 to 12.

9. A method for recovering hairs in tanning for producing leather comprising contacting the treatment solution for use in the unhairing step in tanning for producing leather according to claim 2 with a raw hide or skin and recovering the removed hairs.

10. A method for producing a leather comprising conducting the enzymatic unhairing treatment according to claim 7 in the unhairing step in tanning for producing leather.

* * * * *